(12) United States Patent
Muraki

(10) Patent No.: US 9,063,089 B2
(45) Date of Patent: Jun. 23, 2015

(54) OPTICAL MEASURING APPARATUS, FLOW CYTOMETER, AND OPTICAL MEASURING METHOD

(75) Inventor: Yosuke Muraki, Tokyo (JP)

(73) Assignee: SONY CORPORATION, Tokyo (JP)

( * ) Notice: Subject to any disclaimer, the term of this patent is extended or adjusted under 35 U.S.C. 154(b) by 477 days.

(21) Appl. No.: 13/597,390

(22) Filed: Aug. 29, 2012

(65) Prior Publication Data

US 2013/0056656 A1 Mar. 7, 2013

(30) Foreign Application Priority Data

Sep. 7, 2011 (JP) ................. 2011-194897

(51) Int. Cl.
*G01N 21/53* (2006.01)
*G01N 21/64* (2006.01)
*G01N 15/14* (2006.01)
*G01N 15/10* (2006.01)

(52) U.S. Cl.
CPC .... *G01N 21/6428* (2013.01); *G01N 2015/1006* (2013.01); *G01N 15/1459* (2013.01)

(58) Field of Classification Search
CPC .................. G01N 21/6428; G01N 2015/1006; G01N 15/1459

USPC .................................. 250/564; 702/184–186
See application file for complete search history.

(56) References Cited

U.S. PATENT DOCUMENTS

| | | | | |
|---|---|---|---|---|
| 4,665,020 A | * | 5/1987 | Saunders | 435/7.4 |
| 5,367,474 A | * | 11/1994 | Auer et al. | 702/21 |
| 6,542,833 B1 | * | 4/2003 | Nygaard | 702/46 |
| 8,140,300 B2 | * | 3/2012 | Dunne et al. | 702/186 |

FOREIGN PATENT DOCUMENTS

| | | |
|---|---|---|
| JP | 2009-063305 | 3/2009 |
| JP | 2010-256278 | 11/2010 |

* cited by examiner

*Primary Examiner* — Seung C Sohn
(74) *Attorney, Agent, or Firm* — Dentons US LLP

(57) ABSTRACT

Provided is an optical measuring apparatus including a light irradiating unit that irradiates a sample flowing through a flow path with light, a light detecting unit that detects optical information emitted from the sample due to light irradiation by the light irradiating unit, and a rate information adding unit that adds a predetermined display corresponding to a flow amount of the sample per unit time obtained from the optical information to a waveform data graph obtained from the optical information.

9 Claims, 9 Drawing Sheets

10: FLOW CYTOMETER
2: FLOW PATH
11: LIGHT IRRADIATING UNIT
12: LIGHT DETECTING UNIT
13: RATE INFORMATION ADDING UNIT
16: SORTING UNIT
161: VIBRATING UNIT
162: CHARGING UNIT
163: OPPOSITE ELECTRODE
L: LIGHT

1: OPTICAL MEASURING APPARATUS
2: FLOW PATH
11: LIGHT IRRADIATING UNIT
12: LIGHT DETECTING UNIT
13: RATE INFORMATION ADDING UNIT
S: SAMPLE
T: SUBSTRATE
L: LIGHT

FIG. 3
(a)
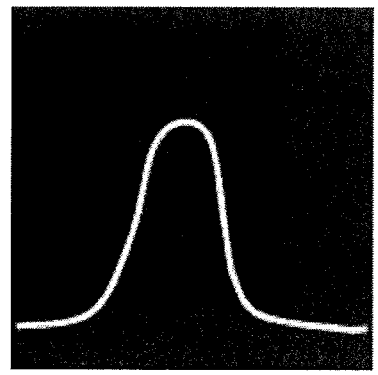
10 event/sec (white)
(b)
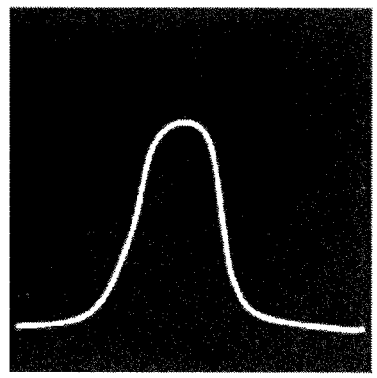
100 event/sec (green)
(c)
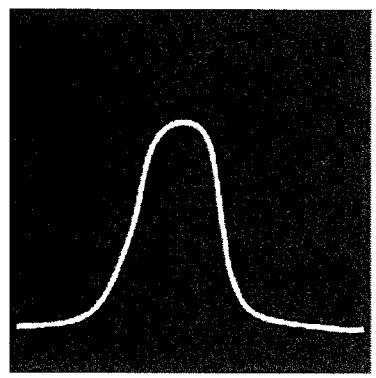
1k event/sec (red)

FIG. 4
(a)
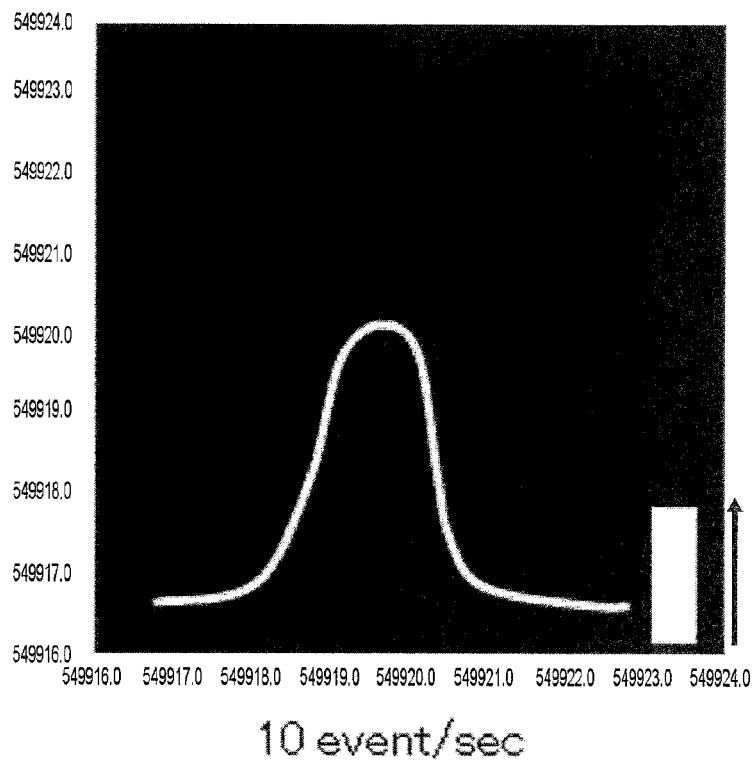
10 event/sec
(b)
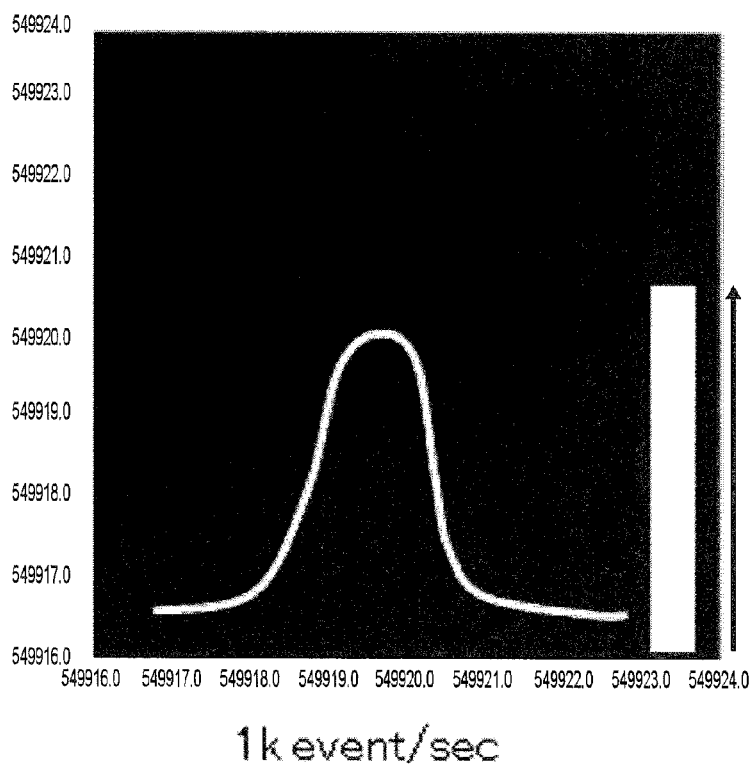
1k event/sec 1k event/sec (no color)    1k event/sec (red)

10: FLOW CYTOMETER
2: FLOW PATH
11: LIGHT IRRADIATING UNIT
12: LIGHT DETECTING UNIT
13: RATE INFORMATION ADDING UNIT
16: SORTING UNIT
161: VIBRATING UNIT
162: CHARGING UNIT
163: OPPOSITE ELECTRODE
L: LIGHT

OPTICAL MEASURING APPARATUS, FLOW CYTOMETER, AND OPTICAL MEASURING METHOD

BACKGROUND

The present technology relates to an optical measuring apparatus that optically detects a sample using a flow path. More particularly, the present disclosure relates to an optical measuring apparatus that optically detects a sample flowing through a flow path, a flow cytometer using the optical measuring apparatus, and an optical measuring method.

In recent years, with the development of analysis techniques, a technique of causing biomicroparticles such as cells or microorganisms or microparticles such as microbeads to flow through a flow path, individually measuring the microparticles in the flow process, analyzing the measured microparticles, and then sorting a desired microparticle has been developed. As a representative example of the technique of analyzing and sorting microparticles using a flow path, an analysis technique called flow cytometry has been rapidly improving.

Flow cytometry refers to an analysis technique in which microparticles are analyzed and sorted such that microparticles of an analysis target flow in a fluid in an aligned state, the microparticles are irradiated with a laser beam, and fluorescent light or scattered light emitted from each microparticle is detected. Processes of flow cytometry are roughly classified into (1) a flow system, (2) an optical system, (3) an electrical analysis system, and (4) a sorting system as follows.

(1) Flow System

In the flow system, microparticles of an analysis target are aligned in a flow cell (flow path). More specifically, a sheath fluid flows into a flow cell at a predetermined speed, and a sample fluid including microparticles slowly flows into a central core of the flow cell in this state. At this time, the fluids do not mix with each other due to the principle of laminar flow, and flow (laminar flow) in which layers form is formed. Inflows of the sheath fluid and the sample fluid are adjusted according to the size of the microparticles of an analysis target or the like, and then the sheath fluid and the sample fluid are caused to flow through in a state in which respective microparticles are aligned.

(2) Optical System

In the optical system, the microparticles of the analysis target are irradiated with light such as a laser, and fluorescent light or scattered light emitted from the microparticles is detected. The flow system (1) causes the microparticles to flow through a laser irradiating unit in a state in which the respective microparticles are aligned. Then, each time each microparticle passes through, fluorescent light or scattered light emitted from the microparticle is detected for each parameter using an optical detector, and a characteristic of each microparticle is analyzed.

(3) Electrical Analysis System

In the electrical analysis system, optical information detected by the optical system is converted into an electric signal (voltage pulse). The converted electric signal is subjected to analog-to-digital (AD) conversion, and a histogram is extracted based on the data through an analysis computer and software, and then analysis is performed.

(4) Sorting System

In the sorting system, the measured microparticles are separated and collected. As a representative sorting technique, there is a technique in which sorting is performed such that positive or negative charges are applied to the measured microparticles, the flow cell is interposed between two deflecting plates having a potential difference therebetween, and so the charged microparticles are attracted to either one of the deflecting plates according to the charges thereof.

Techniques of analyzing and storing the microparticles in the flow path such as flow cytometry have been widely used in various kinds of fields such as the medical field, the drug discovery field, the clinical examination field, the food field, the agricultural field, the engineering field, the forensic medicine field, and the criminal identification field. Particularly, in the medical field, it has undertaken an important role in pathology, tumor immunology, transplantation, genetics, regenerative medicine, chemotherapy, and the like.

The technique of analyzing and storing the microparticles in the flow path is necessary in a very broad range of fields as described above, and techniques related to the processes of (1) to (4) are being developed from day to day. For example, as a technique related to the optical system of (2), Japanese Patent Application Laid-Open (JP-A) No. 2009-063305 discloses a technique in which position information of a sample in a flow path is acquired by irradiating a sample with directional light, and directional light is irradiated based on the position information, so that non-uniform irradiation and deviation of an irradiation position or a focus position are prevented.

Further, Japanese Patent Application Laid-Open No. 2010-256278 discloses a technique in which optical axis alignment is performed such that a detection flow path is positioned with respect to an optical axis of excitation light by controlling movement of a stage with a microorganism examination chip therein based on a quantity of fluorescent light detected by a first detector that detects fluorescent light emitted from a microorganism flowing in the detection flow path and converts the detected fluorescent light into an electric signal.

Meanwhile, optical axis alignment is important in terms of improvement in accuracy to detect a sample flowing through a flow path. Particularly, in recent years, a technique of detecting a cell using a microscale flow path installed in a chip has been developed and put into practical use, and in this lab-on-chip technique, a disposable chip is frequently used. For this reason, how efficiently optical axis alignment is performed each time is very important in terms of improvement in experimental efficiency.

In the related art, when a sample flowing through a flow path is detected, optical axis alignment is performed by observation with an external oscilloscope or while viewing the amplitude of a digital raw waveform or a data plot. In this case, the amplitude of a waveform can be intuitively determined by viewing the waveform, but the frequency of a sample flowing through the flow path can be determined by reading, for example, numerical data (event/sec) of a waveform graph, and optical axis adjustment has to be performed according to the numerical value.

Further, it is difficult to cause samples to flow through in a state in which the respective samples are aligned depending on a degree of the density of samples flowing through the flow path, and when two or more samples flow through in a dense state, an abort rate in which obtained waveform data has two or more peaks may occur. In preventing the abort rate, it is very important to read the frequency of sample flowing through the flow path.

SUMMARY

As described above, in the technique of optically detecting the samples flowing through the flow path, it is very important to read the frequency of the sample flowing through the flow path. However, in actual measurement, in order to recognize the frequency of the sample flowing through the flow path, for example, it is necessary to read numerical data (event/sec) as well as a waveform graph, and optical axis adjustment, density adjustment of a sample, and flow rate adjustment of a sample are performed based on the read numerical value. As described above, since it is difficult to intuitively recognize the frequency of the sample flowing through the flow path, there is a problem in that another operation or measurement efficiency is curtailed.

In this regard, the present disclosure is directed to provide a technique capable of causing the frequency of a sample flowing through a flow path to be intuitively recognized in a technique of optically detecting a sample flowing through a flow path.

As a result of ardent research to achieve the above object, the inventor of this application has reached the present disclosure based on an idea of converting the frequency of a flowing sample into a display other than a numerical value based on detected optical information.

According to an embodiment of the present disclosure, there is provided an optical measuring apparatus which includes a light irradiating unit that irradiates a sample flowing through a flow path with light, a light detecting unit that detects optical information emitted from the sample due to light irradiation by the light irradiating unit, and a rate information adding unit that adds a predetermined display corresponding to a flow amount of the sample per unit time obtained from the optical information onto a waveform data graph obtained from the optical information.

In the optical measuring apparatus according to the present disclosure, the frequency of the flowing sample may be displayed on the waveform data graph, that is, in the waveform data graph.

The optical measuring apparatus according to the present disclosure may further include an optical axis adjusting unit that performs an optical axis adjustment based on rate information added by the rate information adding unit.

In the optical measuring apparatus according to the present disclosure, as long as the frequency of sample can be intuitively recognized, a display added onto the waveform data graph by the rate information adding unit is not particularly limited, and for example, a method of adding a predetermined meter bar or predetermined color information to the waveform data graph may be used.

When predetermined color information is added, the concrete method is not particularly limited, and, for example, a method of adding color information to waveform data or a method of adding color information to the meter bar may be used.

The optical measuring apparatus according to the present disclosure may further include a type information adding unit that adds predetermined color information corresponding to a type of the sample obtained from the optical information to the waveform data graph obtained from the optical information.

The optical measuring apparatus according to the present disclosure can be appropriately used for a flow cytometer and an optical measuring method.

More specifically, a flow cytometer may be configured such that a sorting unit that sorts the sample based on the optical information detected by the light detecting unit is added to the optical measuring apparatus according to the present disclosure.

Here, the terminology used in the present disclosure will be defined. In the present disclosure, a "sample" refers to biomicroparticles such as cells, microorganisms, liposomes, DNA, and protein or any material which can flow through a flow path such as latex particles, gel particles, and synthetic particles such as industrial particles.

According to the embodiments of the present disclosure described above, since the frequency of a flowing sample can be intuitively recognized in a technique of optically detecting a sample flowing through a flow path, various kinds of measurement can be efficiently performed, and the analysis accuracy can be improved.

BRIEF DESCRIPTION OF THE DRAWINGS

FIG. 3 is a graph for describing an example of a method of adding a predetermined display corresponding to a flow amount of a sample per unit time to a waveform data graph, which is performed by a rate information adding unit 13;

FIG. 4 is a graph for describing an example different from that of FIG. 3 as a method of adding a predetermined display corresponding to a flow amount of a sample per unit time to a waveform data graph, which is performed by the rate information adding unit 13;

DETAILED DESCRIPTION OF THE EMBODIMENT(S)

Hereinafter, preferred embodiments of embodying the present disclosure will be described with reference to the accompanying drawings. The following embodiments are exemplary embodiments of the present disclosure, and not intended to cause the scope of the present disclosure to be interpreted in a limited way. The description will proceed in the following order.

1. Optical Measuring Apparatus 1
(1) Flow Path 2
(2) Light Irradiating Unit 11
(3) Light Detecting Unit 12
(4) Rate Information Adding Unit 13
(5) Optical Axis Adjusting Unit 14
(6) Type Information Adding Unit 15
2. Flow Cytometer 10
(1) Sorting Unit 16
3. Optical Measuring Method
(1) Flow Process I
(2) Light Irradiation Process II
(3) Light Detection Process III (4) Rate Information Addition Process IV
(5) Optical Axis Adjustment Process V
(6) Type Information Addition Process VI
(7) Sorting Process VII <1. Optical Measuring Apparatus>

Figure 1:
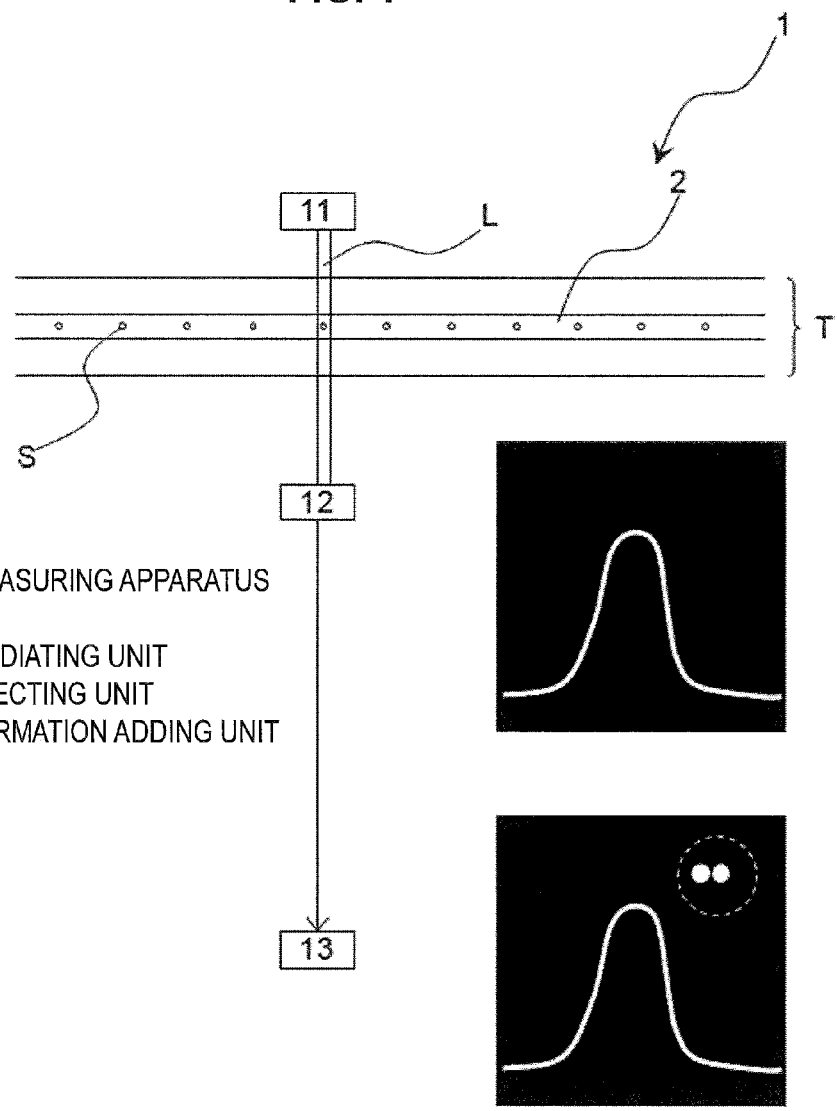
FIG. 1 is a schematic conceptual diagram schematically illustrating a first embodiment of an optical measuring apparatus 1 according to the present disclosure.

FIG. 1 is a schematic conceptual diagram schematically illustrating a first embodiment of an optical measuring apparatus 1 according to the present disclosure.

The optical measuring apparatus 1 according to the present disclosure is an apparatus that optically detects a sample S flowing through a flow path 2, and roughly includes at least a light irradiating unit 11, a light detecting unit 12, and a rate information adding unit 13. Although not shown, the optical measuring apparatus 1 may further include an optical axis adjusting unit 14, a type information adding unit 15, and the like as necessary. The components will be described below in detail.

(1) Flow Path 2

The optical measuring apparatus 1 according to the present disclosure is an apparatus that optically detects the sample S flowing through the flow path 2. The flow path 2 may be installed in the optical measuring apparatus 1 according to the present disclosure in advance. However, for example, a commercially available flow path 2 or a disposable chip having a flow path 2 therein may be installed in the optical measuring apparatus 1, and then measurement may be performed.

The form of the flow path 2 used in the optical measuring apparatus 1 according to the present disclosure is not particularly limited, and can be freely designed. For example, the form of the flow path 2 is not limited to the flow path 2 formed in a two-dimensional or three-dimensional substrate T made of plastic, glass, or the like as illustrated in FIG. 1, and the flow path 2 designed to be used in the flow cytometer of the related art can be used in the optical measuring apparatus 1 according to the present disclosure as in a second embodiment illustrated in FIG. 2.

As long as laminar flow is formed, a flow path width, a flow path depth, and a flow path cross-sectional shape of the flow path 2 are not particularly limited, and can be freely designed. For example, a micro flow path having a flow path width of 1 mm or less can be used in the optical measuring apparatus 1 according to the present disclosure. Particularly, when a micro flow path having a flow path width of about 10 μm or more and 1 mm or less is used, an optical measuring method according to the present disclosure which will be described later can be appropriately performed.

Further, when the flow path 2 formed on the substrate T is employed, it is preferable that a bottom surface of the flow path 2 be made of a material having transparency. In this case, as illustrated in FIG. 1, the light detecting unit 12 (which will be described later) is arranged at an opposite side to the light irradiating unit 11 (which will be described later) with the substrate T interposed therebetween, and thus optical information can be detected from the bottom side of the flow path 2.

(2) Light Irradiating Unit 11

The light irradiating unit 11 is configured to irradiate the sample S flowing through the flow path 2 with light L.

The type of light irradiated from the light irradiating unit 11 is not particularly limited, and light which is constant in light direction, wavelength, and intensity is desirable in order to cause fluorescent light or scattered light to be reliably emitted from the sample S. For example, a laser, a light emitting diode (LED), or the like may be used as the light irradiating unit 11. Here, when the laser is used, the type of laser is not particularly limited, and an argon ion (Ar) laser, a helium-neon (He—Ne) laser, a dye laser, a krypton (Kr) laser, a semiconductor laser, a solid-state laser in which a semiconductor laser is combined with a wavelength conversion optical element, or a laser in which two or more lasers are freely combined may be used.

(3) Light Detecting Unit 12

The light detecting unit 12 is configured to detect optical information emitted from the sample S by light irradiation by the light irradiating unit 11.

As long as optical information is detected, the type of light detecting unit 12 used in the optical measuring apparatus 1 according to the present disclosure is not particularly limited, and any known light detector may be freely selected and employed. For example, a fluorescent light measuring device, a scattered light measuring device, a transmitted light measuring device, a reflected light measuring device, a diffracted light measuring device, an ultraviolet spectroscopic measuring device, an infrared spectroscopic measuring device, a Raman spectroscopic measuring device, a FRET measuring device, a FISH measuring device, various kinds of spectrum measuring devices, a multi-channel light detector in which a plurality of light detectors are arranged in an array form, or a measuring device in which two or more measuring devices are freely combined may be employed.

Figure 2:
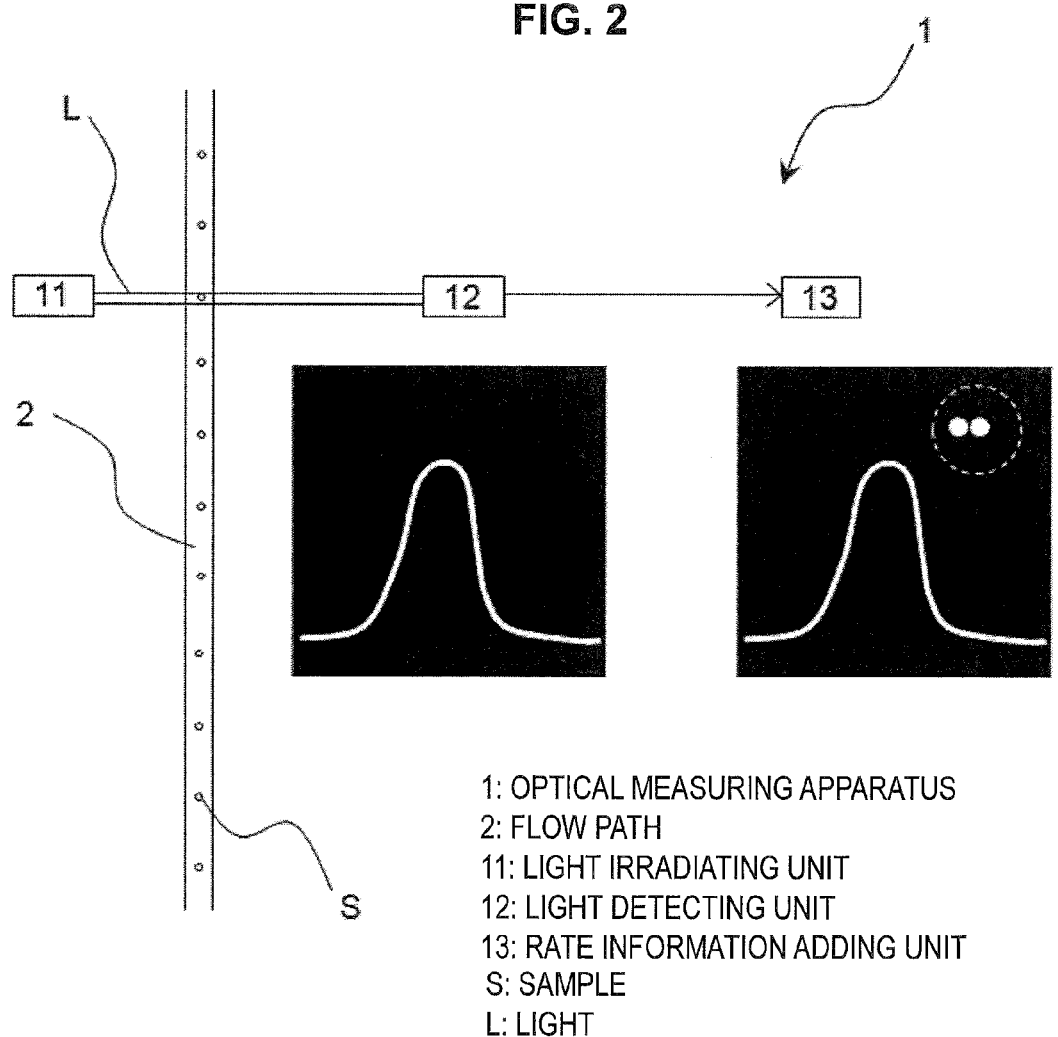
FIG. 2 is a schematic conceptual diagram schematically illustrating a second embodiment of the optical measuring apparatus 1 according to the present disclosure.

Further, in the optical measuring apparatus 1 according to the present disclosure, as long as the optical information emitted from the sample S is detected, an installation position of the light detecting unit 12 is not particularly limited and can be freely designed. For example, when scattered light having a small scattering angle, which is scattered from the sample S, is detected, the light detecting unit 12 is arranged at the opposite side to the light irradiating unit 11 with the flow path 2 interposed therebetween as illustrated in FIGS. 1 and 2. As the light detecting unit 12 is arranged at the opposite side to the light irradiating unit 11 with the flow path 2 interposed therebetween, the light irradiating unit 11 and the light detecting unit 12 can be arranged with a more flexible configuration. Further, for example, when light is also radiated in a direction different from an incident direction of irradiation light such as fluorescent light from the sample S, the light detecting unit 12 may be arranged at the same side as the light irradiating unit 11 or a side which is at an angle of 90° with respect to the light irradiating unit 11 based on the flow path 2.

(4) Rate Information Adding Unit 13

The rate information adding unit 13 is provided to add a predetermined display corresponding to a flow amount of the sample S per unit time obtained from the optical information to a waveform data graph obtained from the optical information. In other words, the rate information adding unit 13 serves to add a predetermined display to the waveform data graph so that the frequency of the sample S flowing through the flow path 2 can be intuitively recognized on the waveform data graph.

Detection of the frequency of the sample S is very important, for example, for optical axis adjustment or sample density adjustment. Specifically, for example, when the frequency of the sample S is lower than the sample density, there is a high possibility that the optical axis will remain deviated. In this case, the optical axis is appropriately adjusted by adjusting the position of the light irradiating unit 11 or the flow path 2, or by adjusting a light irradiation angle of the light irradiating unit 11 or the like such that the frequency of the sample S is equal to the frequency of the sample S estimated from the sample density.

Further, for example, when the frequency of the sample S is high, either the density of the sample S or a sample fluid rate is considered likely to be high. In this case, by decreasing the density of the sample S or adjusting an amount or a speed of a sheath fluid, it is possible to prevent the occurrence of the abort rate in which obtained waveform data has two or more peaks.

As described above, in the optical measuring apparatus 1 according to the present disclosure, the frequency of the sample S which is important in improving the accuracy of each measurement can be intuitively recognized, and thus the efficiency as well as the accuracy of each measurement is significantly improved.

In the optical measuring apparatus 1 according to the present disclosure, as long as the display causes the frequency of the sample S to be intuitively recognized, the display added onto waveform data graph by the rate information adding unit 13 is not particularly limited, and can be freely designed. In the first embodiment and the second embodiment illustrated in FIGS. 1 and 2, a mark ○ is added to the waveform data graph, and the number of marks ○ increases as the frequency of the sample S increases (see dotted line circle parts in FIGS. 1 and 2). However, the display form is not limited to this example.

For example, color information may be added to waveform data according to the frequency of the sample S as illustrated in FIG. 3. In the example illustrated in FIG. 3, when 100 events/sec are exceeded, the waveform data is displayed in green, and when 1000 events/sec are exceeded, the waveform data is displayed in red.

Figure 5:
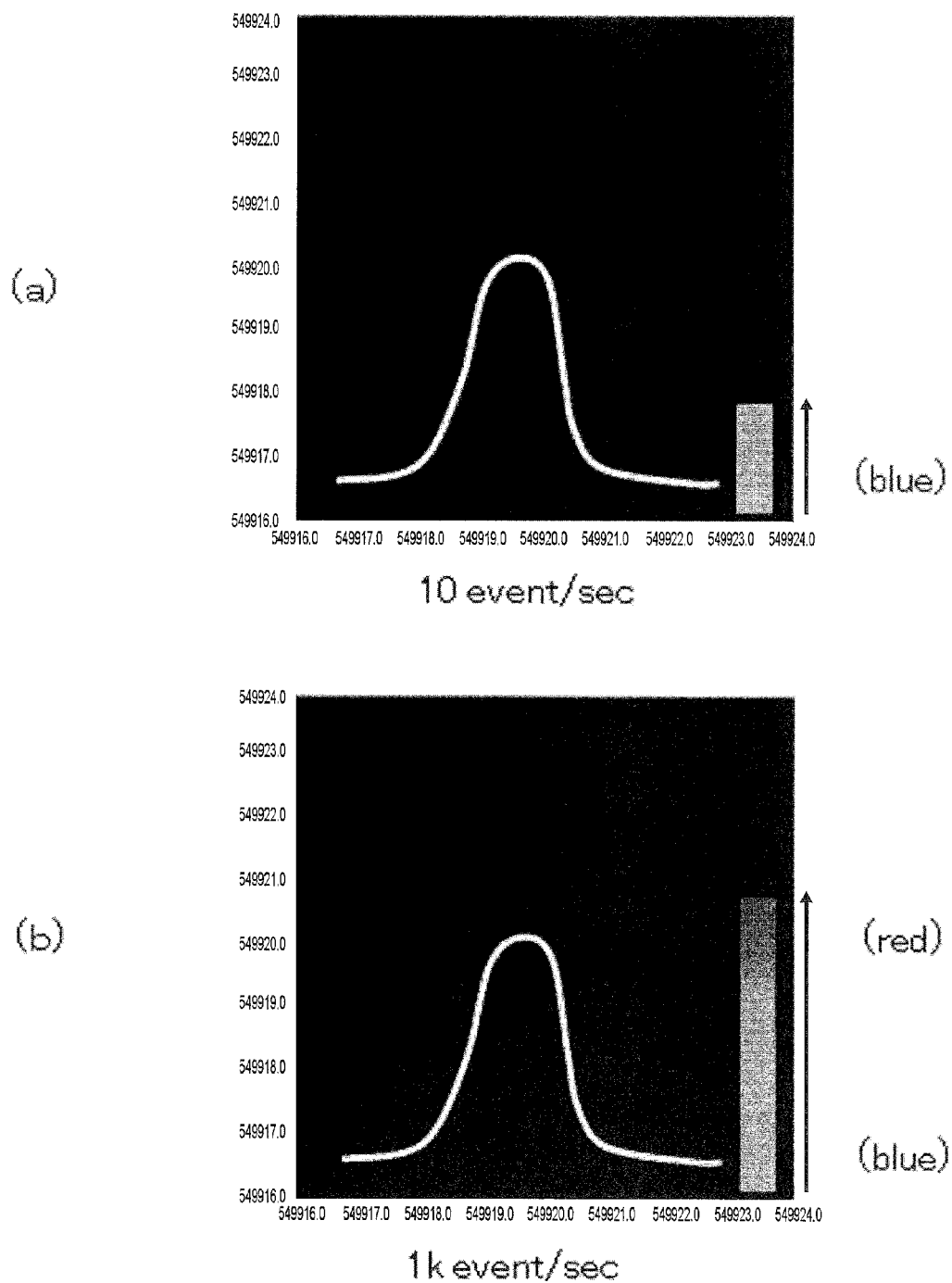
FIG. 5 is a graph for describing an example different from those of FIGS. 3 and 4 as a method of adding a predetermined display corresponding to a flow amount of a sample per unit time to a waveform data graph, which is performed by the rate information adding unit 13.

Further, a predetermined meter bar may be added to the waveform data graph according to the frequency of the sample S as illustrated in FIG. 4. For the sake of easy recognition, color information may be further added to the meter bar according to the frequency of the sample S as illustrated in FIG. 5. FIG. 5 illustrates an example in which blue is added to the meter bar when the frequency of the sample S is low, and red color added to the meter bar when the frequency of the sample S is high.

Figure 6:
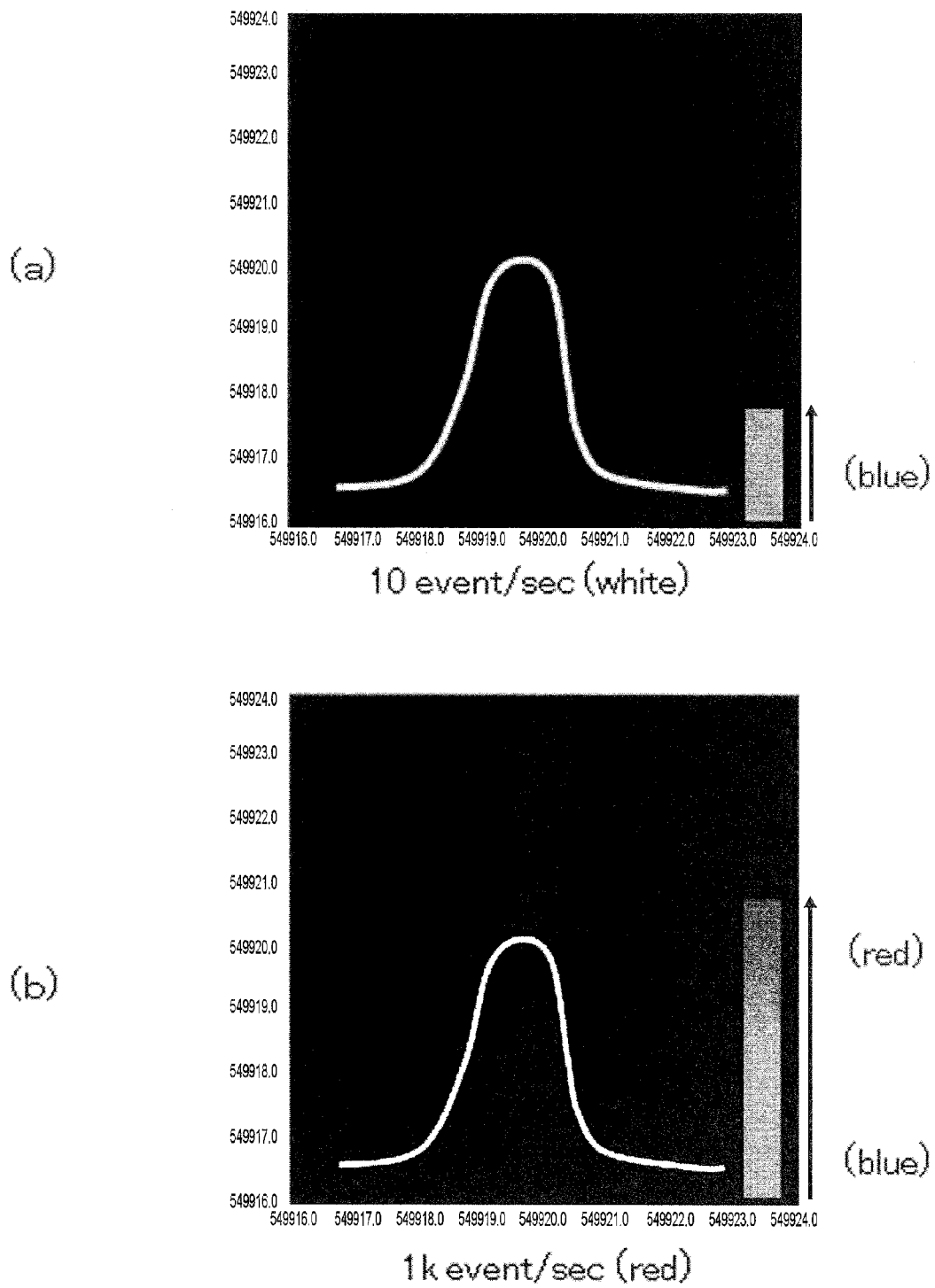
FIG. 6 is a graph for describing an example different from those of FIGS. 3 to 5 as a method of adding a predetermined display corresponding to a flow amount of a sample per unit time to a waveform data graph, which is performed by the rate information adding unit 13.

Further, for the sake of easy recognition, color information may be added to both of the waveform data and the meter bar as illustrated in FIG. 6.

As described above, a display method added to the waveform data graph by the rate information adding unit 13 can be variously designed according to the purpose, and various methods can be freely combined.

(5) Optical Axis Adjusting Unit 14

The optical axis adjusting unit 14 is configured to perform optical axis adjustment based on the rate information added by the rate information adding unit 13. The optical axis adjusting unit 14 is an optional part in the optical measuring apparatus 1 according to the present disclosure, but it is desirable to install the optical axis adjusting unit 14 in order to improve the accuracy of various kinds of measurement.

As long as optical axis adjustment can be performed, a concrete optical axis adjustment method performed by the optical axis adjusting unit 14 is not particularly limited, and can be freely selected and performed. For example, the optical axis may be adjusted such that the light irradiating unit 11 or the flow path 2 is configured to be movable, the position of the light irradiating unit 11 or the flow path 2 is adjusted, or a light irradiation direction or angle of the light irradiating unit 11 is adjusted using a lens, a mirror, or the like.

(6) Type Information Adding Unit 15

The type information adding unit 15 is configured to add predetermined color information corresponding to the type of sample S obtained from the optical information to the waveform data graph obtained from the optical information. In other words, the type information adding unit 15 serves to add predetermined color information to the waveform data graph so that the type of sample S flowing through the flow path 2 can be intuitively recognized on the waveform data graph. The type information adding unit 15 is an optional part in the optical measuring apparatus 1 according to the present disclosure, but it is desirable to install the type information adding unit 15 in order to further improve the accuracy and efficiency of various kinds of measurement.

Figure 7:
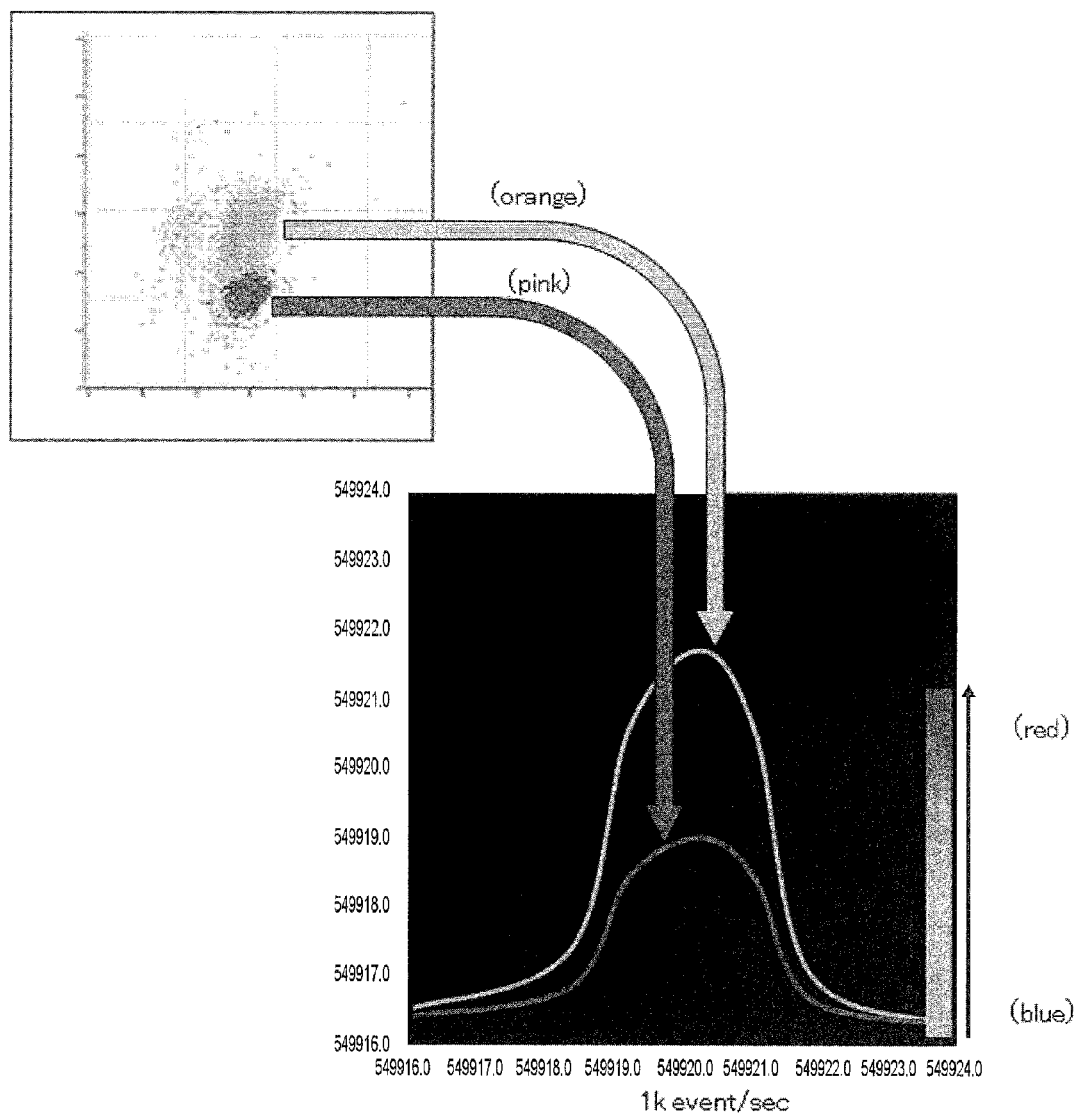
FIG. 7 is a graph illustrating an example of a method of adding predetermined color information corresponding to the type of sample to a waveform data graph, which is performed by a type information adding unit 15.

Specifically, for example, a color to be displayed corresponding to the type of the sample S may be set in advance, the type of sample S may be determined based on the optical information detected by the light detecting unit 12, and color information may be added to the waveform data graph according to the determined type. More specifically, for example, as illustrated in FIG. 7, a certain intensity region may be set to orange, a certain intensity region may be set to pink, and waveform data of the sample S representing intensity in a corresponding region may be colored with a corresponding color based on the optical information detected by the light detecting unit 12.

As described above, the optical measuring apparatus 1 according to the present disclosure is provided with the type information adding unit 15. Thus, even the type as well as the frequency of the sample S can be intuitively recognized, and the efficiency as well as of the accuracy of each measurement can be further significantly improved. For example, in the related art, when eight pink beads are used, it is difficult to make a determination based on raw waveform data, and so data is assigned an ID or the like in advance, and thus desired cell data is linked with row waveform data. However, since the type information adding unit 15 is provided, eight types of colors are added onto the waveform data graph, and thus intuitive reorganization can be made.

In the optical measuring apparatus 1 according to the present disclosure, as long as the color information display causes the type of the sample S to be intuitively recognized, the color information display added to the waveform data graph by the rate information adding unit 13 is not particularly limited, and can be freely designed according to the purpose. In the example illustrated in FIG. 7, color information is added to the waveform data itself, but a target to which color information is added is not limited to this example. For example, color information may be freely added, for example, to the frequency mark (mark o) illustrated in FIGS. 1 and 2, or the meter bar illustrated in FIG. 4.

<2. Flow Cytometer 10>

Figure 8:
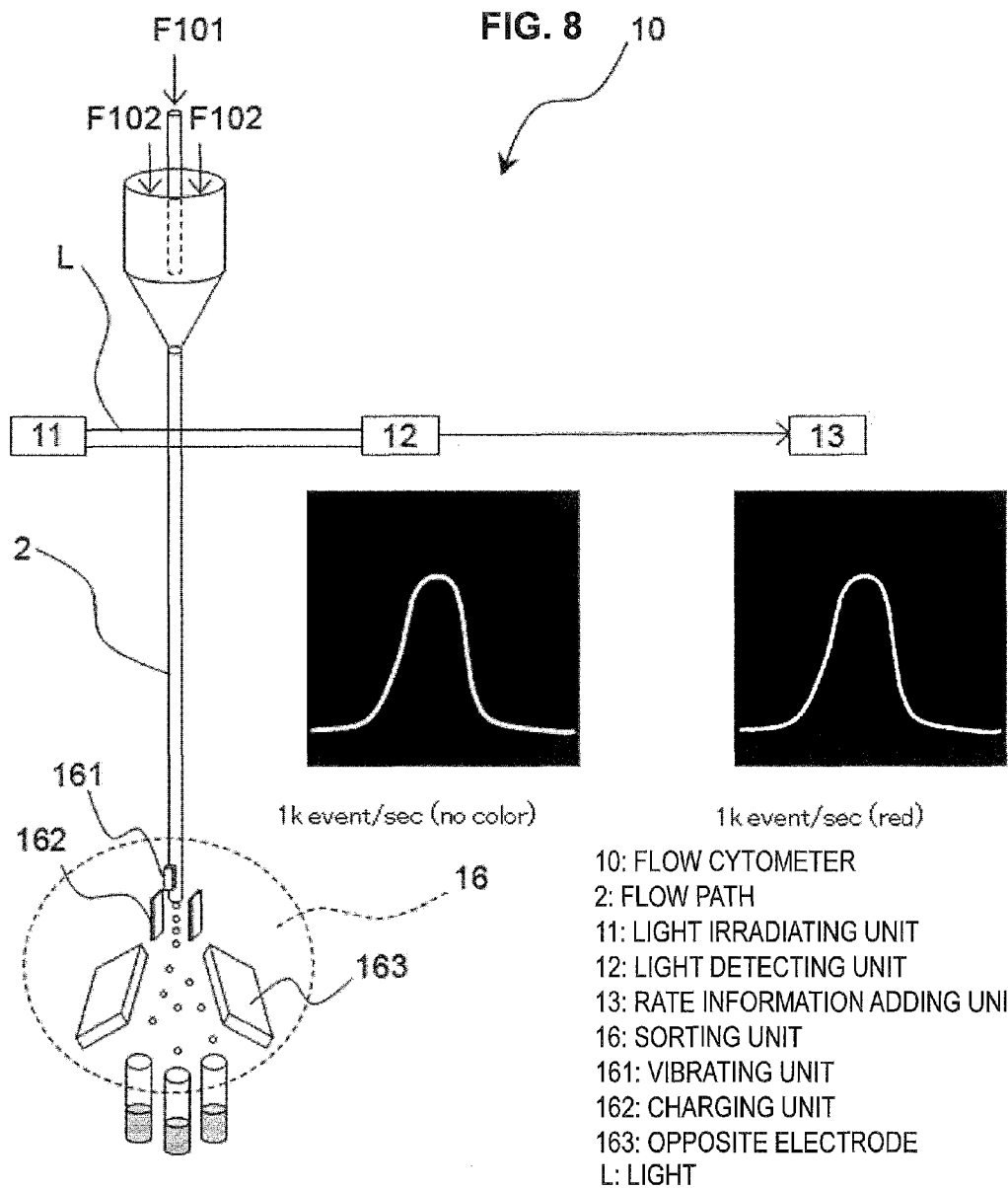
FIG. 8 is a schematic conceptual diagram schematically illustrating an embodiment of a flow cytometer 10 according to the present disclosure.

The optical measuring apparatus 1 according to the present disclosure can be appropriately used for a flow cytometer 10 using the high analysis accuracy and high efficiency. FIG. 8 is a schematic conceptual diagram schematically illustrating an embodiment of the flow cytometer 10 according to the present disclosure.

The flow cytometer 10 according to the present disclosure is an apparatus that optically detects the sample S flowing through the flow path 2, and stores the sample S according to the result, and roughly includes at least a light irradiating unit 11, a light detecting unit 12, a rate information adding unit 13, and a sorting unit 16. Although not shown, the flow cytometer 10 may further include an optical axis adjusting unit 14 and a type information adding unit 15 as necessary. The components will be described below in detail. Here, the light irradiating unit 11, the light detecting unit 12, the rate information adding unit 13, the optical axis adjusting unit 14, and the type information adding unit 15 are the same as in the optical measuring apparatus 1, and thus the redundant description will not be repeated.

(1) Sorting Unit 16

The sorting unit 16 is configured to sort the sample S based on the optical information detected by the light detecting unit 12. For example, the sorting unit 16 sorts the sample S at the downstream side of the flow path 2 based on an analysis result such as the size, the form, and an internal structure of the sample S analyzed based on the optical information.

More specifically, as illustrated in FIG. 8, for example, vibration is applied to the whole or a part of the flow path 2 using a vibrating element 161 that vibrates at a predetermined frequency of vibrations, and so a liquid drop is ejected from an ejecting opening of the flow path 2. In this case, a used vibrating element is not particularly limited, and a known vibrating element can be freely selected and used. For example, a piezo vibrating element may be used. Further, by adjusting an amount of liquid fed to the flow path 2, the diameter of the ejecting opening, the frequency of vibrations of the vibrating element, or the like, the size of a liquid drop can be adjusted, and liquid drops each including a predetermined amount of samples can be generated.

Next, negative or positive charges are applied to the generated liquid drop based on the analysis result such as the size, the form, and an internal structure of the sample S analyzed based on the optical information (see a reference numeral 162 in FIG. 8). Then, sorting is performed such that the course of the charged liquid drop changes to a predetermined direction by opposite electrodes 163 to which a voltage is applied.

<3. Optical Measuring Method>

Figure 9:
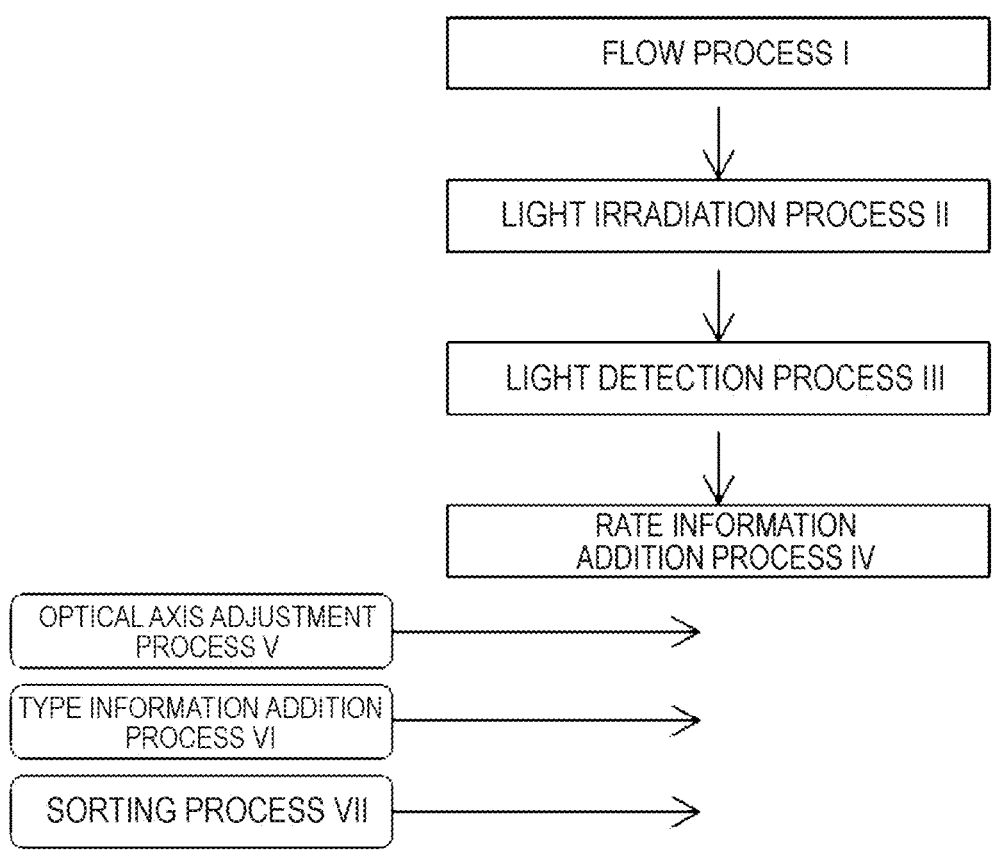
FIG. 9 is a flowchart illustrating an optical measuring method according to the present disclosure.

FIG. 9 is a flowchart illustrating an optical measuring method according to the present disclosure.

The optical measuring method according to the present disclosure roughly includes at least a flow process I, a light irradiation process II, a light detection process III, and a rate information addition process IV. The optical measuring method may further include an optical axis adjustment process V, a type information addition process VI, and a sorting process VII as necessary. The respective processes will be described below in detail.

(1) Flow Process I

The flow process I is a process of causing the sample S to flow through the flow path 2.

A flow method of causing the sample S to flow through the flow path 2 is not particularly limited. For example, a method of carrying fluid media (sheath fluids F102) promoting rectification with a sample fluid F101 including a sample S interposed therebetween may be used as illustrated in FIG. 8. In this case, laminar flow of the sample fluid F101 including the sample S can be formed, and thus the above-described method is appropriate. When the fluid medium has a function of promoting rectification of the sample fluid including the sample S, the type of fluid medium is not particularly limited, but when the sample S is cells, for example, normal saline may be used.

Preferably, the sample S is modified by a mark material such as a fluorescent material such as a fluorescent dye, a radioactive material, an intercalator, or microbeads so that optical information can be detected in the light detection process III which will be described later. For example, when a fluorescent dye is used, the type is not particularly limited, and a known fluorescent dye may be used. For example, cascade blue, pacific blue, fluorescein isothiocyanate (FITC), phycoerythrin (PE), propidium iodide (PI), texas red (TR), peridinin chlorophyll protein (PerCP), allophycocyanin (APC), 4', 6-diamidino-2-phenylindole (DAPI), Cy3, Cy5, Cy7, or a combination of two or more above-mentioned materials may be used.

Further, when the sample S emits light like fluorescent protein, it is unnecessary to modify the sample S with a mark material. Further, for example, when a material that can change a fluorescent color of a material as in the principle of FRET due to the progress of interaction between materials in the flow path 2 is used as the sample S, it is unnecessary to modify the sample S with a mark material.

(2) Light Irradiation Process II

The light irradiation process II is a process of irradiating the sample S flowing through the flow path 2 with light.

In the light irradiation process II, the type of light to irradiate is not particularly limited, and two or more types of light described above in connection with the optical measuring apparatus 1 may be freely combined and used.

(3) Light Detection Process III

The light detection process III is a process of detecting optical information emitted from the sample S flowing through the flow path 2 due to irradiation of the light L in the light irradiation process II using the light detecting unit 12.

In the light detection process III, as long as the optical information from the sample S can be detected, the acquisition method is not particularly limited, and two or more types of methods described above in connection with the optical measuring apparatus 1 may be freely combined and employed.

(4) Rate Information Addition Process IV

In the rate information addition process IV, a predetermined display corresponding to a flow amount of the sample S per unit time obtained from the optical information is added to the waveform data graph obtained from the optical information. In other words, the rate information addition process IV is a process of adding a predetermined display to the waveform data graph so that the frequency of the sample S flowing through the flow path 2 can be intuitively recognized in the waveform data graph. The concrete rate information adding method performed in the rate information addition process IV and the effects thereof are the same as in the optical measuring apparatus 1, and thus the redundant description will not be repeated.

(5) Optical Axis Adjustment Process V

In the optical axis adjustment process V, optical axis adjustment is performed based on the rate information added in the rate information addition process IV. The optical axis adjustment process V is an optional process in the optical measuring method according to the present disclosure, and it is desirable to perform the optical axis adjustment process V to further improve the accuracy of each measurement. The concrete optical axis adjustment method performed in the optical axis adjustment process V and the effects thereof are the same as in the optical measuring apparatus 1, and thus the redundant description will not be repeated.

(6) Type Information Addition Process VI

In the type information addition process VI, predetermined color information corresponding to the type of sample S obtained from the optical information is added to the waveform data graph obtained from the optical information. In other words, the type information addition process VI is a process of adding predetermined color information to the waveform data graph so that the type of sample S flowing through the flow path 2 can be intuitively recognized on the waveform data graph. The type information addition process VI is an optional process in the optical measuring method according to the present disclosure, but it is desirable to perform the type information addition process VI in order to further improve the accuracy and efficiency of various kinds of measurement. The concrete type information adding method performed in the type information addition process VI and the effects thereof are the same as in the optical measuring apparatus 1, and thus the redundant description will not be repeated.

(7) Sorting Process VII

The sorting process VII is a process of sorting the sample S based on the optical information detected in the light detection process III. In the present disclosure, the sorting process VII is an optional process, but when the sorting process VII is performed, the optical measuring method according to the present disclosure can be performed as a process of flow cytometry. For example, in the sorting process VII, the sample S is sorted at the downstream side of the flow path 2 based on the analysis result such as the size, the form, and an internal structure of the sample S analyzed based on the optical information. The concrete sorting method performed in the sorting process VII is the same as in the optical measuring apparatus 1, and thus the redundant description will not be repeated.

According to the present disclosure, in a technique of optically detecting a sample flowing through a flow path, the frequency or the type of the sample flowing through the flow path can be intuitively recognized based on optical information obtained from the sample, and thus the analysis accuracy and the efficiency can be improved. Using this technique can contribute to improvement in an analysis technique in various kinds of fields such as the medical field (pathology, tumor immunology, transplantation, genetics, regenerative medicine, chemotherapy, and the like), the drug discovery field, the clinical examination field, the food field, the agricultural field, the engineering field, the forensic medicine field, and the criminal identification field.

It should be understood by those skilled in the art that various modifications, combinations, sub-combinations and alterations may occur depending on design requirements and other factors insofar as they are within the scope of the appended claims or the equivalents thereof.

The present disclosure contains subject matter related to that disclosed in Japanese Priority Patent Application JP 2011-194897 filed in the Japan Patent Office on Sep. 7, 2011, the entire content of which is hereby incorporated by reference.

What is claimed is:

1. An optical measuring apparatus, comprising:
    a light irradiating unit that irradiates a sample flowing through a flow path with light;
    a light detecting unit that detects optical information emitted from the sample due to light irradiation by the light irradiating unit; and
    a rate information adding unit that adds a predetermined display corresponding to a flow amount of the sample per unit time obtained from the optical information to a waveform data graph obtained from the optical information.

2. The optical measuring apparatus according to claim 1, further comprising
    an optical axis adjusting unit that performs an optical axis adjustment based on rate information added by the rate information adding unit.

3. The optical measuring apparatus according to claim 1, wherein the rate information adding unit adds a predetermined meter bar according to a flow amount of the sample per unit time obtained from the optical information.

4. The optical measuring apparatus according to claim 1, wherein the rate information adding unit adds predetermined color information according to a flow amount of the sample per unit time obtained from the optical information.

5. The optical measuring apparatus according to claim 4, wherein the rate information adding unit adds the color information to waveform data.

6. The optical measuring apparatus according to claim 4, wherein the rate information adding unit adds the color information to a meter bar.

7. The optical measuring apparatus according to claim 1, further comprising
    a type information adding unit that adds predetermined color information corresponding to a type of the sample obtained from the optical information to the waveform data graph obtained from the optical information.

8. A flow cytometer comprising:
    a light irradiating unit that irradiates a sample flowing through a flow path with light;
    a light detecting unit that detects optical information emitted from the sample due to light irradiation by the light irradiating unit;
    a rate information adding unit that adds a predetermined display corresponding to a flow amount of the sample per unit time obtained from the optical information to a waveform data graph obtained from the optical information; and
    a sorting unit that sorts the sample based on the optical information detected by the light detecting unit.

9. An optical measuring method, comprising:
causing a sample to flow through a flow path;
irradiating the sample with light;
detecting optical information emitted from the sample due to light irradiation in the irradiating of the sample; and
adding a predetermined display corresponding to a flow amount of the sample per unit time obtained from the optical information to a waveform data graph obtained from the optical information.

* * * * *